United States Patent
Remijan

(10) Patent No.: US 10,806,689 B2
(45) Date of Patent: Oct. 20, 2020

(54) COSMETIC FORMULATION

(71) Applicant: Freck Yourself, Inc., Los Angeles, CA (US)

(72) Inventor: Christine Remijan, Los Angeles, CA (US)

(73) Assignee: Freck Yourself, Inc., Los Angeles, CA (US)

( * ) Notice: Subject to any disclaimer, the term of this patent is extended or adjusted under 35 U.S.C. 154(b) by 0 days.

(21) Appl. No.: 16/359,771

(22) Filed: Mar. 20, 2019

(65) Prior Publication Data

US 2019/0290571 A1    Sep. 26, 2019

Related U.S. Application Data

(60) Provisional application No. 62/646,258, filed on Mar. 21, 2018.

(51) Int. Cl.

| | | |
|---|---|---|
| A61K 8/81 | (2006.01) |
| A61K 8/34 | (2006.01) |
| A61K 8/19 | (2006.01) |
| A61K 8/9789 | (2017.01) |
| A61K 8/41 | (2006.01) |
| A61Q 1/10 | (2006.01) |
| A61Q 1/02 | (2006.01) |
| A61Q 1/12 | (2006.01) |
| A61K 8/49 | (2006.01) |
| A61K 8/44 | (2006.01) |
| A61K 8/36 | (2006.01) |

(52) U.S. Cl.
CPC .............. *A61K 8/8147* (2013.01); *A61K 8/19* (2013.01); *A61K 8/345* (2013.01); *A61K 8/36* (2013.01); *A61K 8/44* (2013.01); *A61K 8/498* (2013.01); *A61K 8/9789* (2017.08); *A61Q 1/025* (2013.01)

(58) Field of Classification Search
None
See application file for complete search history.

(56) References Cited

U.S. PATENT DOCUMENTS

| | | | | |
|---|---|---|---|---|
| 2007/0286824 A1* | 12/2007 | Rabe | ...................... | A61Q 19/00 424/59 |
| 2013/0022562 A1* | 1/2013 | Maunsell | .................. | A61K 8/97 424/59 |
| 2013/0192624 A1* | 8/2013 | Florence | .................. | A61K 8/97 132/200 |

* cited by examiner

*Primary Examiner* — Kyung S Chang
(74) *Attorney, Agent, or Firm* — Trojan Law Offices

(57) ABSTRACT

The present invention features cosmetic compositions and a method for pigmentations that create realistic and long-wearing freckles on a user's skin. These compositions include advantages such as being applicable to various skin types. Other advantages include resistance to smearing and a more realistic appearance superior to alternative faux freckle solutions. These compositions can also be applied using various apparatuses.

10 Claims, 5 Drawing Sheets

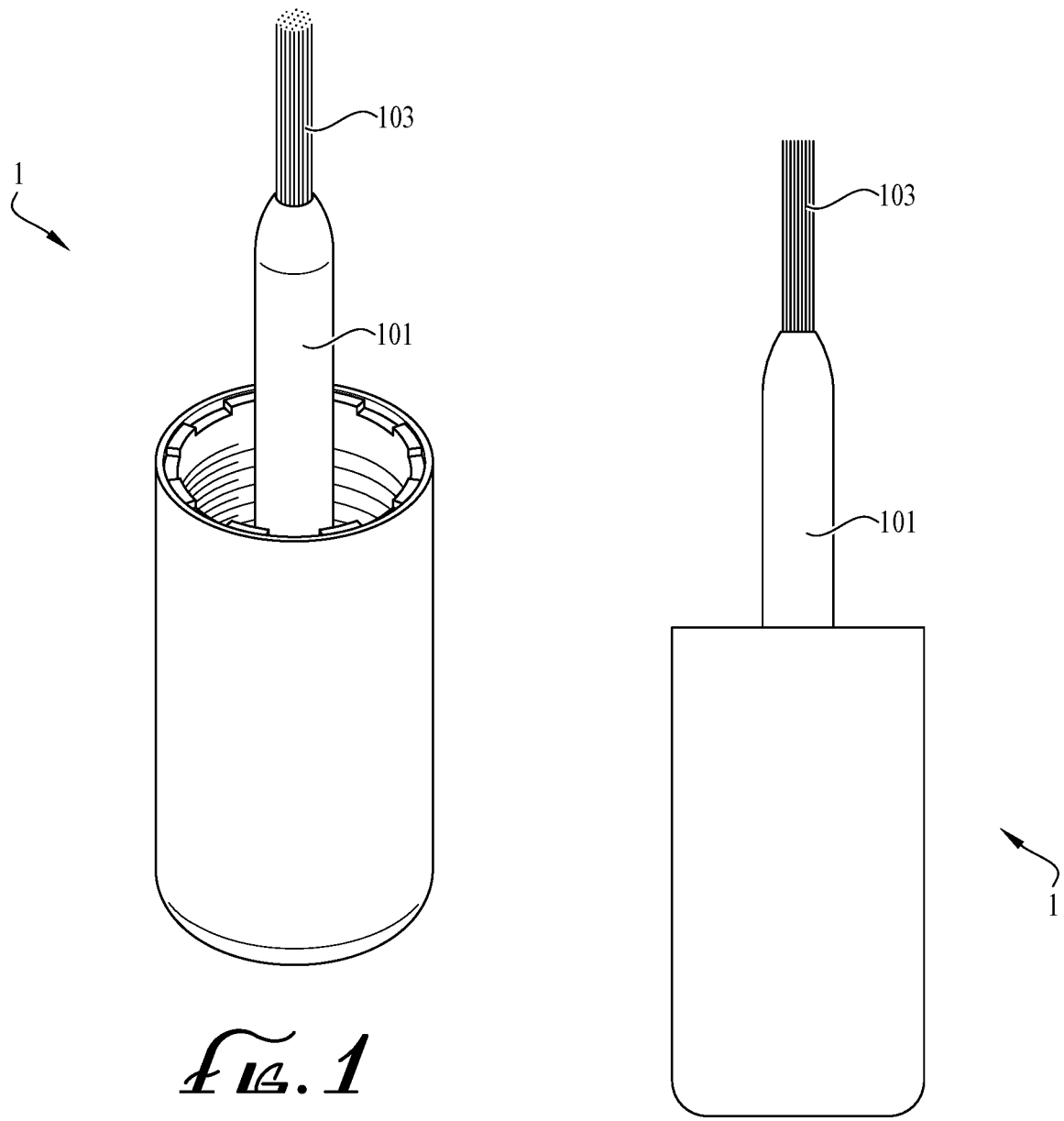

COSMETIC FORMULATION

CROSS-REFERENCE TO RELATED APPLICATIONS

The application claims priority to and benefit of U.S. Provisional Patent Application No. 62/646,258, filed on Mar. 21, 2019, the content of which is incorporated by reference in its entirety.

FIELD OF THE INVENTION

The present invention relates to a freckle cosmetic composition, and more particularly, to a freckle cosmetic composition for topical application to create realistic and all day cosmetic freckles.

BACKGROUND OF THE INVENTION

Applying cosmetic products on a user's skin to create a "faux-freckle look" has become a new area of interest for the growing cosmetic industry. Typically, faux-freckle products are difficult to use because they require a steady hand to apply properly on the user's skin and the result is frequently unrealistic and can easily smear.

For example, makeup artists have been using other pigments (i.e. eyebrow products, eyeshadows, eyeliners, or lipsticks) and tools (i.e. toothpicks, spoolies, and pencils) to create the look of faux freckles. But each of these approaches do not address the problem of the freckles appearing unrealistic or address the difficulty of the freckles smearing. One of the faux-freckle products on the market, Topshop's freckle pencil, is a two-toned eyeliner that creates uniform circles on the face and body. Because of the uniform circles, the product applied on the user's skin does not look realistic. In addition, because of the waxy consistency of the eyeliner, the product does not work well with all kinds of skin types. For example, users with oily skin type do not accept waxy substances to the skin well.

The object of the present invention is to invent a product with a brush and gel formula and a procedure for its use that effectively provides a freckle cosmetic composition that forms realistic freckles capable of being worn all day without significant smearing.

SUMMARY OF THE INVENTION

In accordance with the objectives of the invention, there is provided a freckle cosmetic composition comprising: i. from about 85 to about 95% by weight water; ii. less than 1% by weight polyacrylic acid; iii. less than 1% by weight glycerin; iv. less than 1% by weight a colorant; v. less than 0.1 to about 1% by weight a pH adjuster; vi. less than 1% by weight a preservative; vii. less than 1% by weight a chelating agent. In one embodiment, the colorant further comprises red pigments from about 0.1% to about 1% by weight, blue pigments from about 0.01 to about 0.08% by weight, and yellow pigments from about 0.05 to about 0.1% by weight. In one embodiment, the pH adjuster is sodium hydroxide.

In one embodiment of the present invention, there is provided a method of creating long wear cosmetic freckles. The method comprises applying a freckle cosmetic composition on a user's skin by an applicator, forming three to five hemispheres on the user's skin with three to seven seconds. In one embodiment, the user blots the hemispheres in their center within seven to thirty seconds of forming the hemispheres to form a freckle shape on the skin, and repeats the formation of hemispheres and blots until the desired number of freckles have been formed.

These and other objects, advantages, and features of the invention will be more fully understood and appreciated by reference to the detailed description of the current embodiments and the drawings.

BRIEF DESCRIPTION OF THE DRAWINGS

FIG. 1 illustrates a perspective front view of an embodiment of the applicator of the invention.

FIG. 2 illustrates a side view of an embodiment of the applicator of the invention.

DETAILED DESCRIPTION OF EMBODIMENTS

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and to fully convey the scope of the invention to those skilled in the art.

The formula of a freckle cosmetic composition is to create a long-wear freckles on all types of skin, even on an oily skin type. Long-wear in this context means all day without significant smearing. Due to the specific ingredients, the freckle cosmetic composition applied on the skin will not drift away throughout the day.

Accordingly, the formulations of the present invention are particularly valuable to users because they form natural-looking freckles, which are neither too perfect in circumference or too jagged or shapeless. The formulations also give the appearance of translucence or depth to the freckle thereby mimicking the appearance of natural freckles, and avoiding the one-dimensional appearance of painted on dots common with the prior art. The present formulations described herein also permit variations in color, darkness, and size from one freckle to another, which improves the natural appearance of the faux freckles over the prior art.

Figure 3:
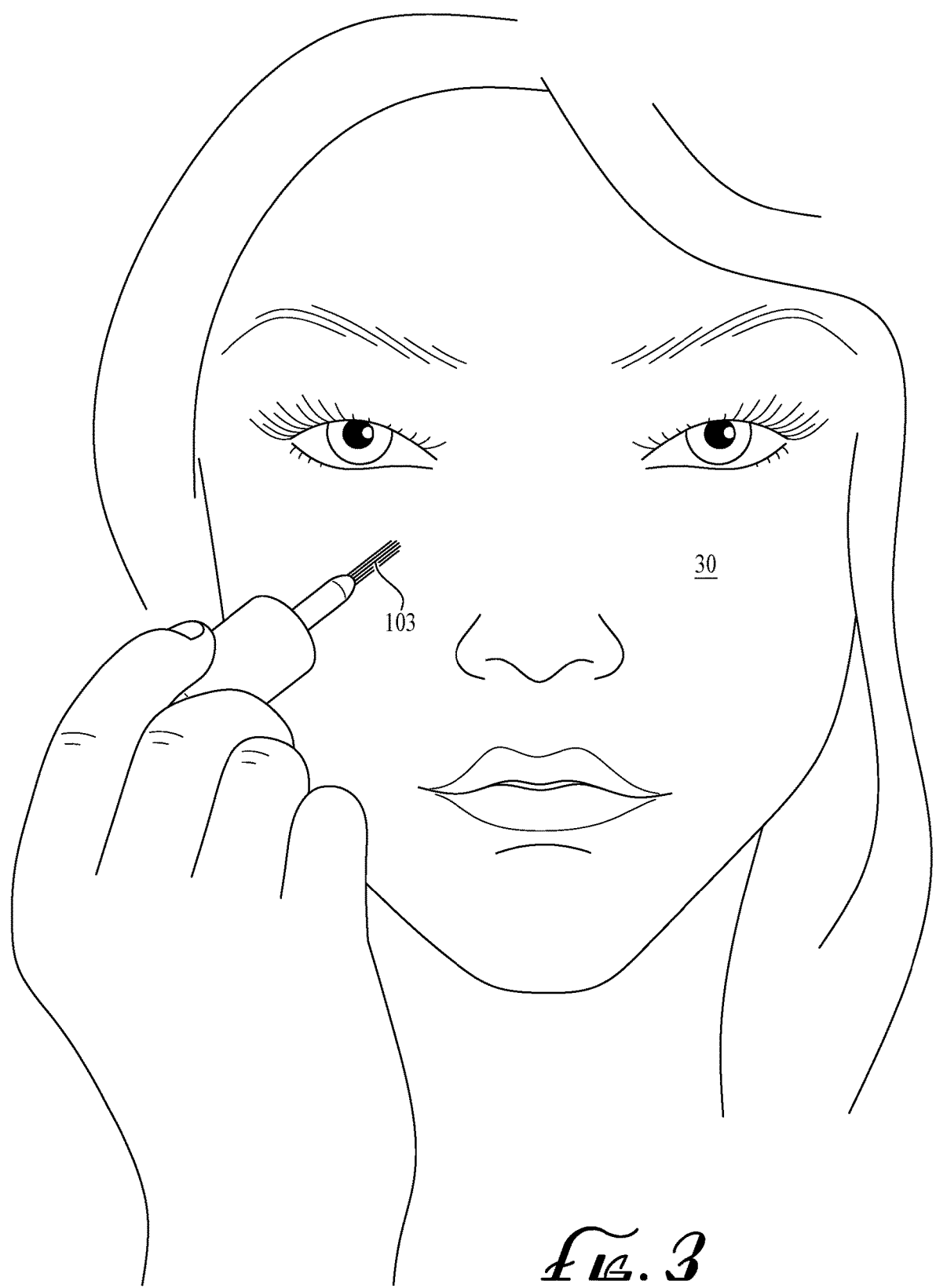
FIG. 3 illustrates a perspective view of the method of applying the cosmetic composition to the user's skin.
Figure 4:
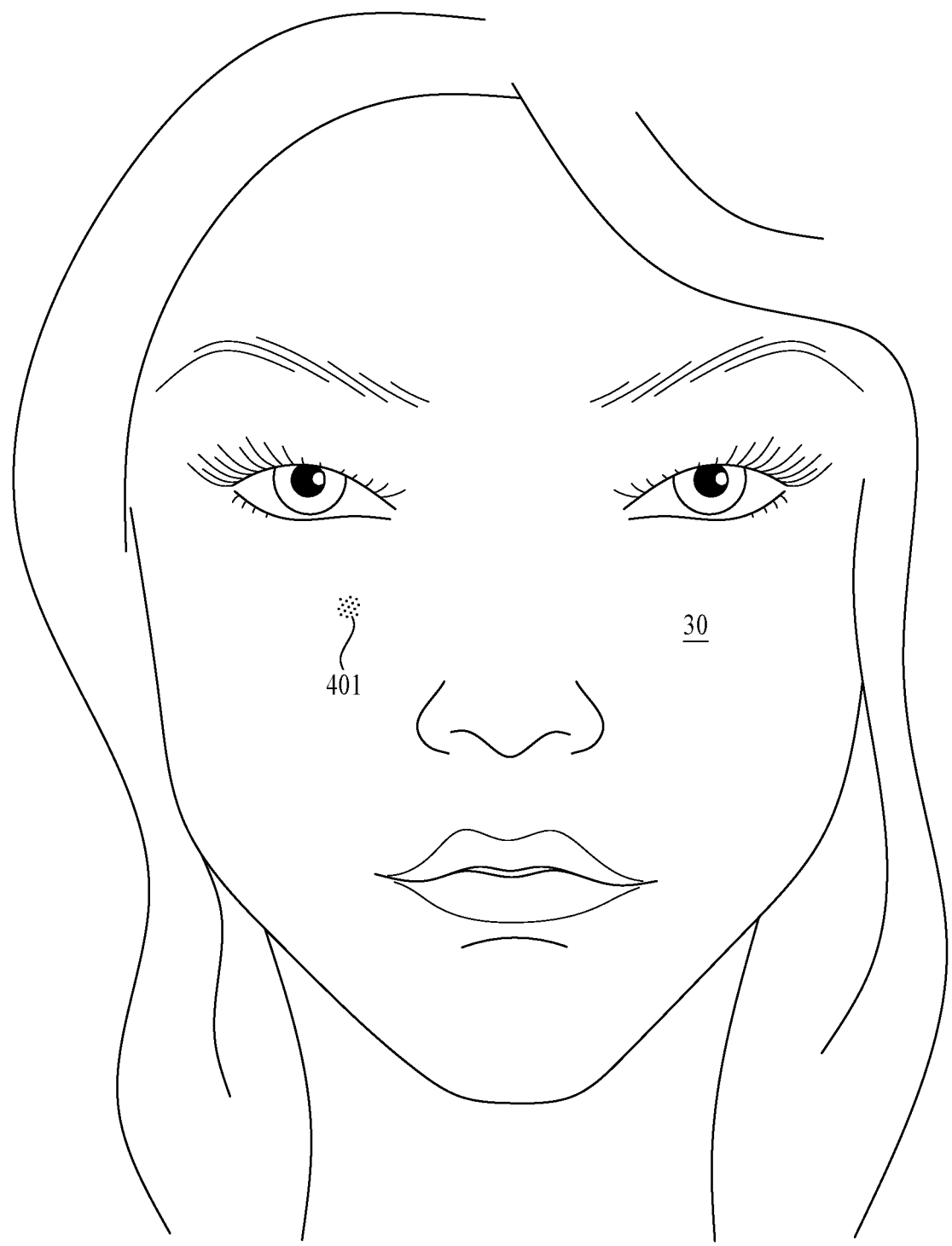
FIG. 4 illustrates a perspective view of the method of applying the cosmetic composition to the user's skin, forming a hemisphere shape on the user's skin.

The formulation of the preferred embodiment is most effective if applied to the skin using a specific procedure. The first step in the procedure is to employ a customized applicator for the formulation. As shown in FIG. 1 and FIG. 2, in a preferred embodiment, the customized applicator 1 has a conventional handle 101 to which approximately 100 bristles 103 are secured. The range of bristles 103 used in the applicator can be from 75 to 125 bristles. Each bristle 103 in the preferred embodiment is approximately eight millimeters in length. The bristles 103 are bound together tightly, and regardless of the length of the bristles chosen for an applicator, it is important that all of the bristles 103 in a specific applicator 1 be of substantially uniform length so that the formulation can be applied to the surface of the user's skin 30 to form a hemisphere 401, as shown in FIG. 3 and FIG. 4. The number and length of the bristles in the preferred embodiment insures that the hemisphere 401 does not smear and avoids stray bristles 103 from forming lines of the formulation. The length for the bristles 103 can range downward to approximately five millimeters, but the upper range to the length of the bristles 103 should not significantly exceed eight millimeters. If stiffer bristles are used, then it is possible to lengthen the bristles to ten to twelve millimeters. However, the stiffer bristles are not preferred because there needs to be some resilience in the bristles at the ends to effectively form a proper hemisphere.

In the preferred embodiment for the applicator, the length of the bristles is important because standard make up brushes, such as eyeliner brushes, are intended to bend so that makeup is applied in strokes that take advantage of the makeup on the sides of the bristles. Referring now to FIG. 3, in the applicator for present method, it is undesirable for the bristles 103 to bend too much because it will smear the formulation and form lines. To address this issue, the bristles 103 are kept within the range of the preferred length and number.

Figure 5:
FIG. 5 illustrates a perspective view of the method of applying the cosmetic composition to the user's skin.
Figure 6:
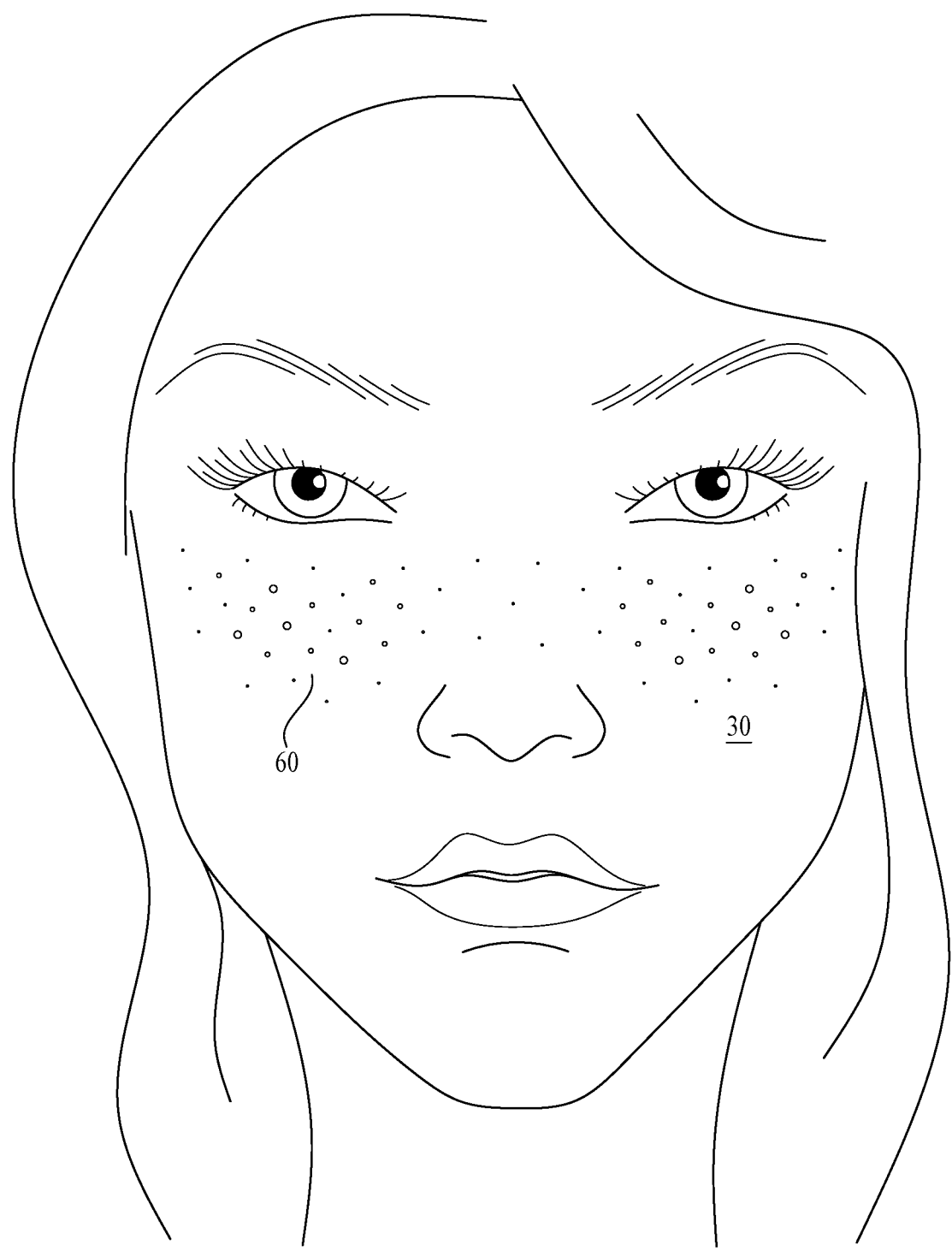
FIG. 6 illustrates a perspective view of the user's face having faux freckles.

Referring now to FIG. 5, once the hemisphere 401 of the formulation is formed on the surface of the skin 30, the user blots 50 the hemisphere 401 with the user's finger 501 to form the final freckle. The blotting process 50 should be applied directly down to the center of the hemisphere 401 to form a proper freckle shape. As shown in FIG. 6, the excess of formulation on the finger can be applied to other areas of the skin 30 to form other freckles 60 of varying sizes and darkness in order to create the natural appearance of a field of freckles 60 on the surface of the skin 30. A makeup sponge could be used in place of a finger, but the use of a finger is the most effective method for forming freckles.

As shown in FIG. 4, FIG. 5 and FIG. 6, the timing of the application of each hemisphere 401 of formulation is important to the proper procedure for forming freckles. The applicator should be used to apply no more than approximately five to eight hemispheres at a time with ten hemispheres being at the upper limit. This should take approximately three to seven seconds. The blotting procedure 50 should start with the first applied hemisphere, as shown in FIG. 5. The range of times to begin blotting after application of the hemispheres 401 is from seven seconds to 30 seconds. The timing of the blotting procedure 50 should correspond to the desired darkness of the freckles given the skin tone and preferences of the user. Once the first set of freckles have been applied, the procedure above can be repeated.

Components of the Cosmetic Compositions

Polyacrylic acid. The compositions of the present invention comprise a polyacrylic acid, which is used as a thickener:

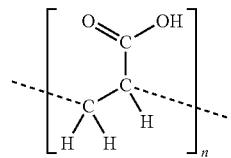

In one embodiment, the compositions also include acrylic acid. Cosmetic formulation of the present invention usually comprises less than 1% by weight of polyacrylic acid.

Glycerin. Glycerin is a natural compound found in animal- and plant-derived fats, which play as a moisturizer in alleviating a user's skin's problem. Cosmetic formulation of the present invention comprises less than 1% by weight of glycerin, having the structure:

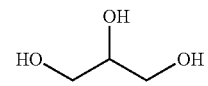

A pH Adjuster. The pH adjuster is a white crystalline odorless solid that absorbs moisture from the air and adjusts the pH of the present invention. Cosmetic formulation of the present invention comprises less than 1% by weight of the pH adjuster. In a preferred embodiment, the pH adjuster is sodium hydroxide (NaOH).

A preservative. The preservative is a chemical that is added to products, including pharmaceutical drugs or cosmetics to prevent decomposition by microbial growth or by undesirable chemical changes. Cosmetic formulation of the present invention comprises less than 1% by weight of the preservative. In some embodiments, the preservative can be potassium sorbate:

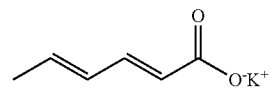

In some embodiments, the preservative can be sodium dehydroacetate:

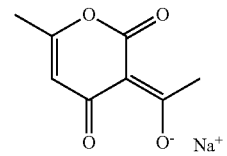

A chelating agent. The chelating agent are chemical compounds that react with metal ions to form a stable, water-soluble complex. In a preferred embodiment, the chelating agent is tetrasodium EDTA:

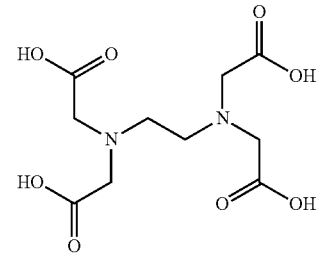 [SMILES: O=C(O)CN(CCN(CC(=O)O)CC(=O)O)CC(=O)O]

In one embodiment, the freckle cosmetic compositions comprise a colorant, which is added to change the color of a material. The colorant of the present invention is used for coloring the user's skin, for the purpose of coloring the user's skin. In one embodiment, the colorant comprises three different pigments in the compositions: red, blue, and yellow. The red pigments further comprise from about 0.1% to about 1% by weight of the colorant. The blue pigments comprise from about 0.01% to about 0.08% by weight of the colorant. The yellow pigments comprise from about 0.05% to about 0.1% by weight of the colorant.

Example 1 and 2 illustrates topical compositions according to the present invention. The composition can be processed in a conventional manner. They are suitable for cosmetic use. In particular, the cosmetic compositions are suitable for creating realistic freckles on the user's skin.

Freckle Cosmetic Composition

Example 1

| NAME | % (w/w) |
| --- | --- |
| WATER | 85-95% |
| POLYACRYLIC ACID | <1% |
| ROSA CENTIFOLIA FLOWER WATER | 4-10% |
| GLYCERIN WATER | <1% |
| COLORANT (RED) | 0.01-0.08% |
| COLORANT (BLUE) | 0.1-1.0% |
| COLORANT (YELLOW) | 0.05-0.1% |
| SODIUM HYDROXIDE | <1% |
| POTASSIUM SORBATE | <1% |
| SODIUM DEHYDROACETATE | <1% |
| TETRASODIUM EDTA | <1% |
| TOTAL | 100% |

Example 2

| NAME | % (w/w) |
| --- | --- |
| WATER | 85-95% |
| POLYACRYLIC ACID | <1% |
| ACRYLIC ACID | <1% |
| ETHYL ACETATE | <1% |
| ROSA CENTIFOLIA FLOWER WATER | 4-10% |
| GLYCERIN WATER | <1% |
| COLORANT (RED) | 0.01-0.08% |
| COLORANT (BLUE) | 0.1-1.0% |
| COLORANT (YELLOW) | 0.05-0.1% |
| SODIUM HYDROXIDE | <1% |
| POTASSIUM SORBATE | <1% |
| SODIUM DEHYDROACETATE | <1% |
| TETRASODIUM EDTA | <1% |
| TOTAL | 100% |

While illustrative embodiments of the invention have been described in detail above, it is to be understood that the appended claims are intended to be construed to include variations of the present invention.

What is claimed is:

1. A freckle cosmetic composition for topical application, consisting of:
   from about 85 to about 95% by weight water;
   less than 1% by weight polyacrylic acid;
   less than 1% by weight glycerin;
   less than 1% by weight a colorant consisting of red pigments from about 0.1 to about 1% by weight, blue pigments from about 0.01 to about 0.08% by weight, and yellow pigments from about 0.05 to about 0.1% by weight;
   less than 1% by weight a pH adjuster;
   less than 1% by weight a preservative; and
   less than 1% by weight a chelating agent wherein all of the said ingredients are present together in the freckle cosmetic composition.

2. The freckle cosmetic composition for topical application of claim 1, wherein the water comprises rose water.

3. The freckle cosmetic composition for topical application of claim 1, wherein said pH adjuster is Sodium Hydroxide.

4. The freckle cosmetic composition for topical application of claim 1, wherein said preservative is potassium sorbate.

5. The freckle cosmetic composition for topical application of claim 1, wherein said preservative is sodium dehydroacetate.

6. The freckle cosmetic composition for topical application of claim 1, wherein said chelating agent is tetrasodium EDTA.

7. A freckle cosmetic composition for topical application, consisting of:
   from about 85 to about 95% by weight water;
   less than 1% by weight polyacrylic acid;
   less than 1% by weight glycerin;
   less than 1% by weight a colorant consisting of red pigments from about 0.1 to about 1% by weight, blue pigments from about 0.01 to about 0.08% by weight, and yellow pigments from about 0.05 to about 0.1% by weight;
   less than 1% by weight Sodium Hydroxide;
   less than 1% by weight potassium sorbate; and
   less than 1% by weight tetrasodium EDTA wherein all of the said ingredients are present together in the freckle cosmetic composition.

8. A method of creating long wear cosmetic freckles, comprising:
   applying the freckle cosmetic composition of claim 1 or claim 7 on a user's skin by an applicator, forming three to five hemispheres on said user's skin with three to seven seconds;
   blotting said hemispheres in their center within seven to thirty seconds of forming said hemispheres to form a freckle shape on said skin; and,
   repeating the formation of hemispheres and blotting until the desired number of freckles have been formed.

9. The method of creating long wear cosmetic freckles of claim 8, wherein said freckle shape can vary in sizes and darkness by the user's finger.

10. The method of creating g wear cosmetic freckles of claim 8, wherein materials of said bristles of said applicator is soft to create resilience such that said hemisphere can be created on said user's skin.

* * * * *